(12) United States Patent
Bertollo et al.

(10) Patent No.: US 11,666,734 B2
(45) Date of Patent: Jun. 6, 2023

(54) MICRONEEDLE BASED STABILISATION SYSTEM FOR MEDICAL DEVICES

(71) Applicant: University College Dublin, National University of Ireland, Dublin, Dublin (IE)

(72) Inventors: Nicky Bertollo, Dublin (IE); Seamus Morris, County Dublin (IE); Eoin O'Cearbhaill, County Dublin (IE)

(73) Assignee: UNIVERSITY COLLEGE DUBLIN, NATIONAL UNIVERSITY OF IRELAND, DUBLIN, Dublin (IE)

(*) Notice: Subject to any disclaimer, the term of this patent is extended or adjusted under 35 U.S.C. 154(b) by 116 days.

(21) Appl. No.: 17/048,275

(22) PCT Filed: Apr. 16, 2019

(86) PCT No.: PCT/EP2019/059779
§ 371 (c)(1),
(2) Date: Oct. 16, 2020

(87) PCT Pub. No.: WO2019/201903
PCT Pub. Date: Oct. 24, 2019

(65) Prior Publication Data
US 2021/0060302 A1    Mar. 4, 2021

(30) Foreign Application Priority Data

Apr. 17, 2018    (GB) ...................................... 1806246

(51) Int. Cl.
*A61M 25/02*    (2006.01)

(52) U.S. Cl.
CPC ..... *A61M 25/02* (2013.01); *A61M 2025/0286* (2013.01)

(58) Field of Classification Search
CPC .... A61M 2025/0286; A61M 2025/024; A61M 2025/028
See application file for complete search history.

(56) References Cited

U.S. PATENT DOCUMENTS

| 4,164,943 A | 8/1979 | Hill et al. | |
| 5,470,321 A * | 11/1995 | Forster | A61M 25/02 604/174 |

(Continued)

FOREIGN PATENT DOCUMENTS

WO    9316751 A1    9/1993

*Primary Examiner* — Theodore J Stigell
*Assistant Examiner* — Rachel T. Smith
(74) *Attorney, Agent, or Firm* — Tarolli, Sundheim, Covell & Tummino L.L.P.

(57) ABSTRACT

A stabilisation system for securing a medical device such as a catheter to tissue, in particular skin, the stabilisation system comprising a main body having a first section and a second section displaceable relative to one another to translate the system between an undeployed state and a deployed state, each section including an array of microneedles extending from a tissue contacting surface of the body and which penetrate the skin in response to the above displacement, the stabilisation system further comprising a closure member displaceable between an open position exposing a retention zone on the body and a closed position at least partially occluding the retention zone, within which retention zone the catheter or other medical device may be captured.

23 Claims, 14 Drawing Sheets

(56) References Cited

U.S. PATENT DOCUMENTS

2009/0054843 A1* 2/2009 Lundqvist ............ A61M 25/02
                                                      604/177
2013/0053629 A1* 2/2013 Franklin ............... A61F 5/0056
                                                       600/37

* cited by examiner

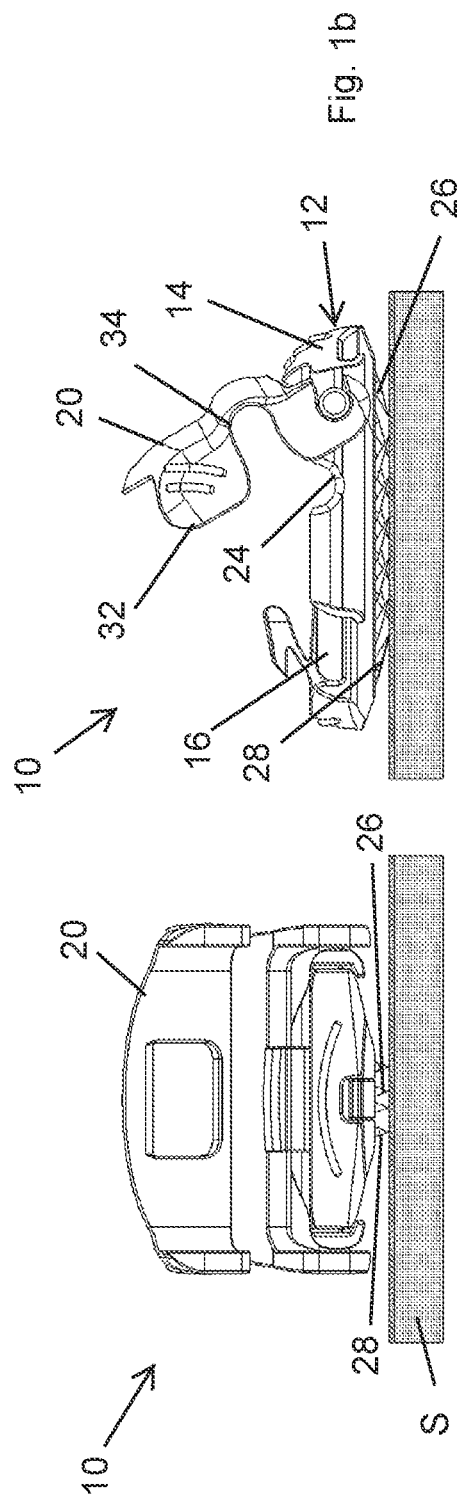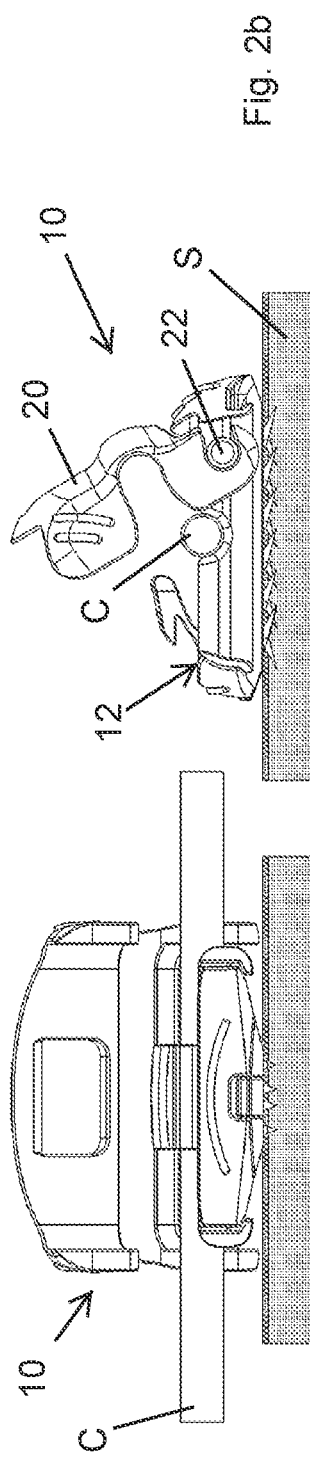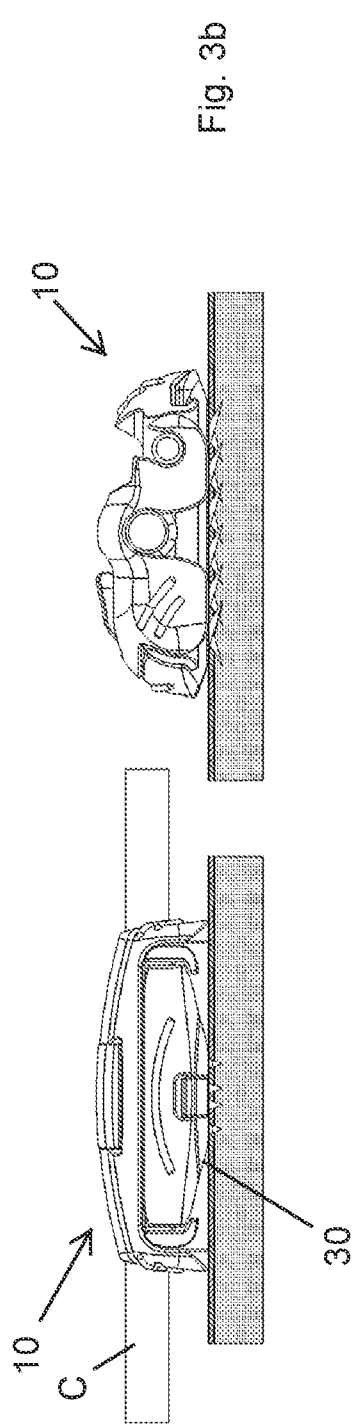

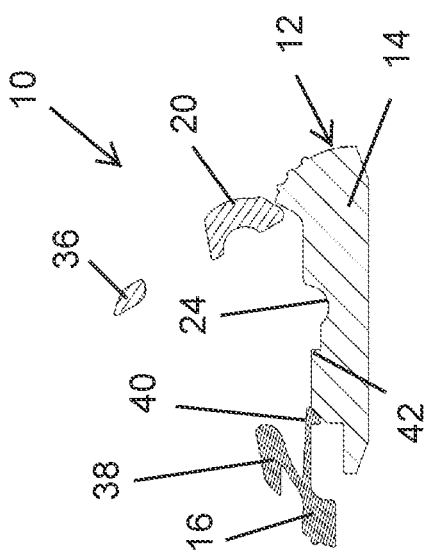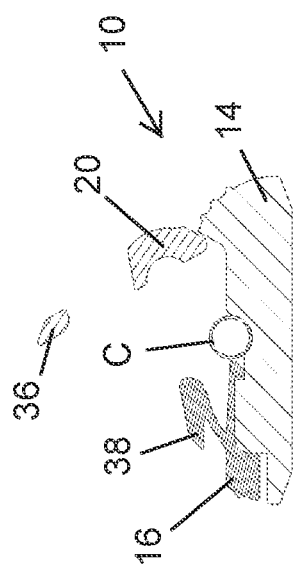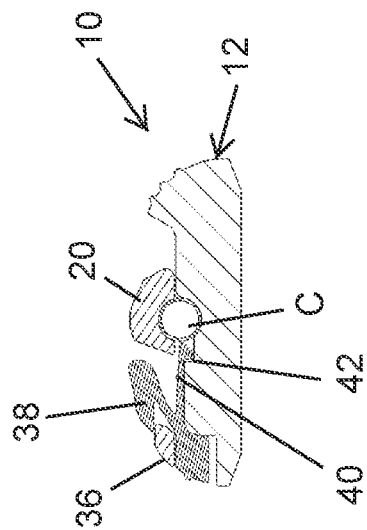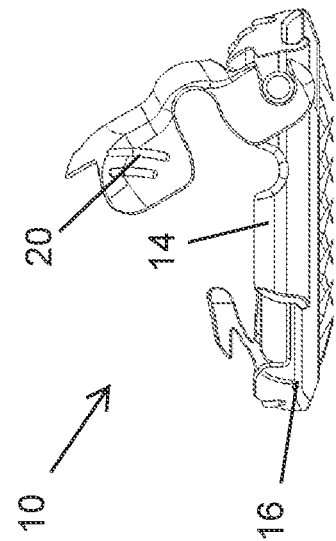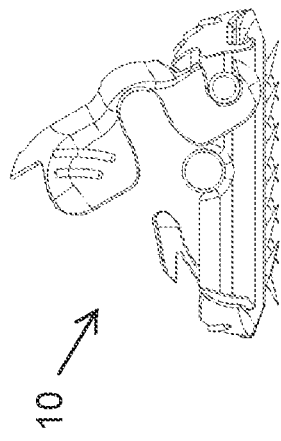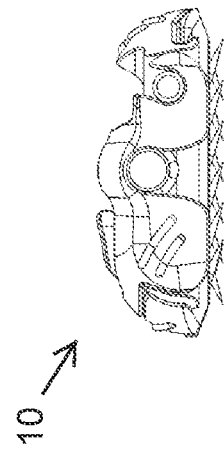

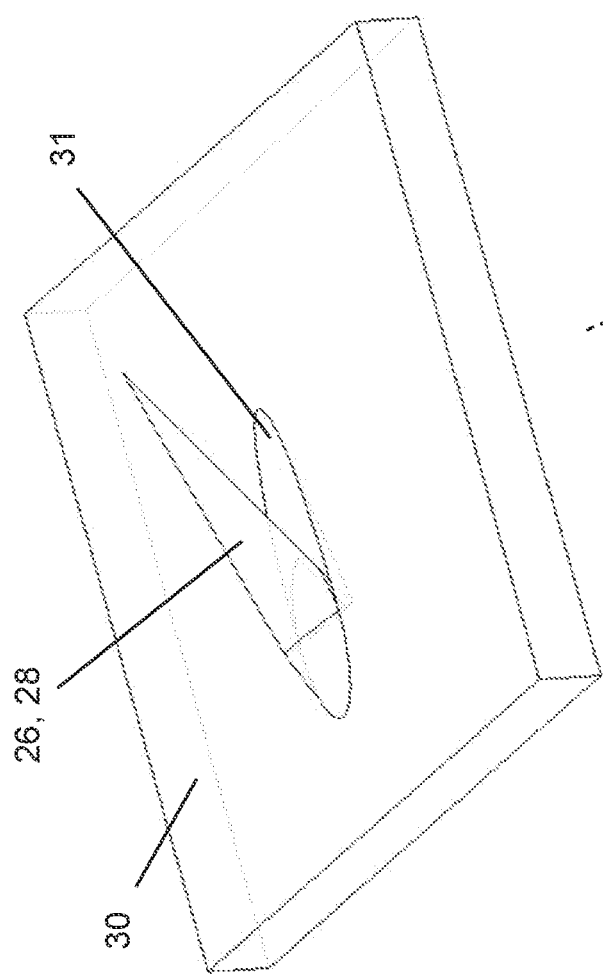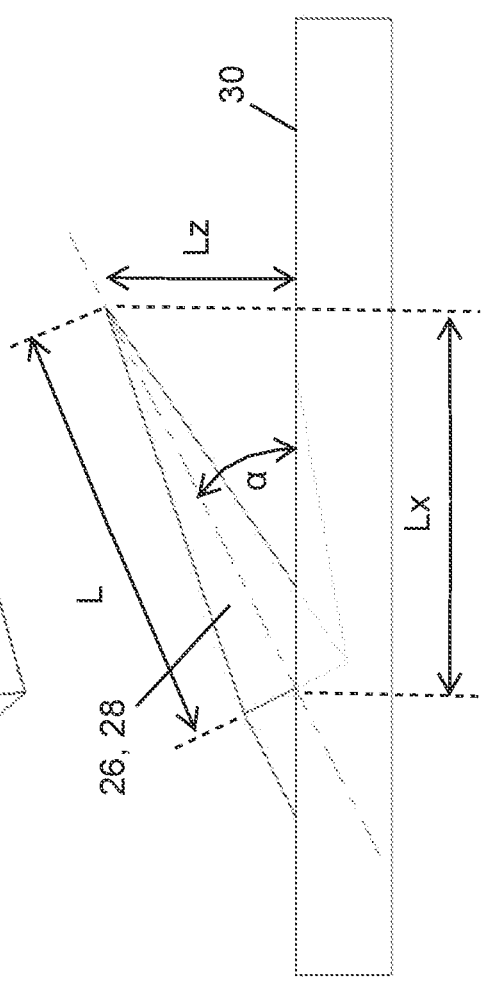

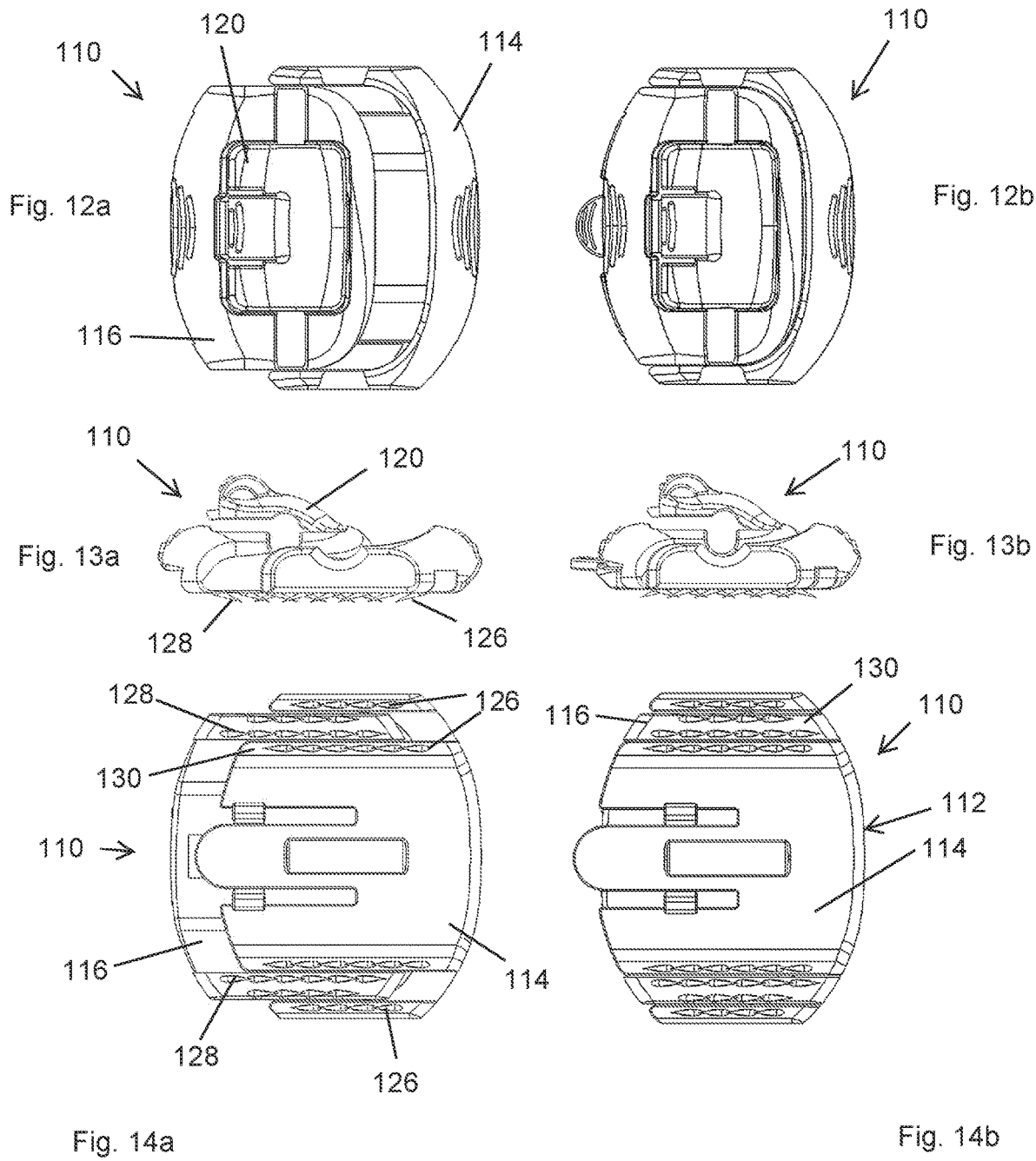

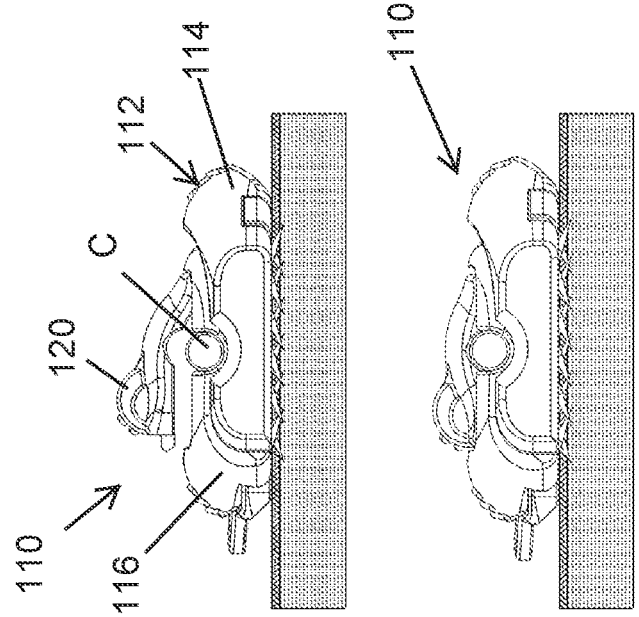

MICRONEEDLE BASED STABILISATION SYSTEM FOR MEDICAL DEVICES

RELATED APPLICATIONS

The present invention is a U.S. National Stage under 35 USC 371 patent application, claiming priority to Ser. No. PCT/EP2019/059779, filed on 16 Apr. 2019; which claims priority of GB 1806246.3, filed on 17 Apr. 2018, the entirety of both of which are incorporated herein by reference.

FIELD OF THE INVENTION

The present invention is concerned with a stabilisation system for medical devices, in particular but not exclusively for anchoring medical devices such as catheters or the like to the skin or other tissue substrate of a patient in order to prevent the catheter from being dislodged when tension or other destabilising forces are applied to the catheter or other medical device.

BACKGROUND OF THE INVENTION

In a significant number of medical procedures, and during periods of monitoring or convalescence of patients, it is necessary to securely anchor various forms of medical device to the patient, and at various anatomical sites which may vary in size, shape, surface conditions, etc. One of the most common forms of device to be so anchored is a catheter, which are commonly used to deliver or drain fluids from the patient, in addition to acting as a guide conduit for various other interventional medical devices such as stent delivery systems, etc.

In both cases it is often critical that the catheter or other medical device is not inadvertently tensioned or displaced, as this may lead to a loss of function and resulting complications for the patient or treatment being administered.

While there are numerous known systems for securing catheters or the like to a patient, these prior art systems often require the use of straps, Velcro® or adhesive to be applied to the skin, which can be difficult and time consuming to apply, in particular depending on the location on the body at which the anchor is required to be located. Tensioning straps to adequately secure the device in position can put undue pressure on the surrounding tissue and can be uncomfortable for the patient, potentially chaffing the surrounding tissue, and creating general discomfort. The efficacy of adhesives can vary significantly depending on the condition of the patient's skin, and has a tendency to degrade over time.

It is therefore an object of the present invention to provide a robust yet simple stabilisation system for securing a medical device to a tissue substrate.

SUMMARY OF THE INVENTION

According to a first aspect of the present invention there is provided a stabilisation system for securing medical devices to tissue comprising a main body having a first section and a second section displaceable relative to one another to translate the system between an undeployed state and a deployed state; at least one protrusion projecting from the first section and at least one protrusion projecting from the second section; and a closure member displaceable between an open position exposing a retention zone on the body and a closed position at least partially occluding the retention zone.

Preferably, at least one protrusion on at least one section is inclined towards the at least one protrusion on the other section.

Preferably, the first and second section are displaceable relative to one another in a first direction and the at least one protrusion on the first section and the second section overlap in a second direction substantially perpendicular to the first direction when the anchor is in the deployed state.

Preferably, the first section and the second section each define a tissue contacting surface from which the respective at least one protrusion extends.

Preferably, the tissue contacting surface is convex.

Preferably, the tissue contacting surface of the first section and/or the second section comprises a recess located at or adjacent a root of the respective at least one protrusion.

Preferably, the stabilisation system comprises one or more feet which are disposed outboard of the protrusions and are shaped and dimensioned to contact a tissue substrate on which the stabilisation device is deployed.

Preferably, the stabilisation system comprises a pair of feet, one located on either side of the protrusions.

Preferably, the one or more feet are provided on the closure member.

Preferably, the stabilisation system comprises a lock operable to releasably secure the closure member in the closed position.

Preferably, the lock is operable to fix the first and second sections relative to one another.

Preferably, the closure member comprises a guideway shaped and dimensioned to bias the medical device towards the retention zone as the closure member is displaced from the open to the closed position.

Preferably, the retention zone comprises an elongate channel.

Preferably, the elongate channel extends in a direction substantially perpendicular to the first direction.

Preferably, the elongate channel extends in a direction substantially parallel to the first direction.

Preferably, the elongate channel extends in a direction substantially perpendicular to the first and the second directions.

Preferably, the first section defines a slot adapted to at least partially receive the second section therein.

Preferably, the body is configured such that the at least one protrusion on the first section and the second section overlap in the second direction when the body is in the deployed state.

Preferably, each protrusion comprises a microneedle.

Preferably, the protrusions on both the first and second sections are arranged in a rectangular array.

Preferably, the body is at least partially formed from a porous material.

Preferably, the stabilisation system comprises an aperture extending through the body such as to allow a medical component to extend through the stabilisation system from a tissue substrate on which the stabilisation system is deployed.

Preferably, the closure member is defined by at least a portion of the first section and/or at least a portion of the second section.

According to a second aspect of the present invention there is provided a method of securing a medical device to tissue with a stabilisation system, the method comprising the steps of inserting at least one protrusion projecting from a first section of a body of the stabilisation system and at least one protrusion projecting from a second section of the stabilisation system into the tissue; displacing the first section relative to the second section to translate the stabilisation system from an undeployed state to a deployed state, wherein the at least one protrusion on the first section and the second section effect localised deformation of the tissue surrounding the protrusions when the body is in the deployed state; locating the medical device at least partially within a retention zone on the body before, during or after displacing the stabilisation system into the deployed state; and displacing a closure member of the stabilisation system from an open position exposing the retention zone to a closed position at least partially occluding the retention zone before, during, after or as part of displacing the stabilisation system into the deployed state such as to secure the medical device to the stabilisation system.

Preferably, the stabilisation system comprises two sets of first and second sections, the method comprising the step of displacing the first and second sections of one set relative to one another in a first direction from the undeployed to the deployed state, and the further step of displacing the first and second sections of the other set relative to one another in a second direction from the undeployed to the deployed state.

Preferably, the two sets of first and second sections are spaced apart and connected to one another by a bridging element.

Preferably, the method comprises the step of displacing one set of first and second sections in a direction perpendicular to the direction of displacement of the other set.

As used herein, the term "micro feature" or "microneedle" is intended to mean a feature or needle/barb which is of a particular dimension, generally in the range of 100-3,000 micrometres (μm) in length or height, and may include for example a "microneedle" which can be used as a barb and/or as a combined barb and drug delivery or bio-sensing system.

As used herein, the term "retention zone" is intended to mean a zone, area or coupling into which a medical device such as a catheter or the like may be located, or which may be adapted to be releasably or permanently connected with a coupling provided on or as part of the medical device.

As used herein, the term "closure member" is intended to mean one or more parts or components, or a portion of one or more larger parts or components, which may be displaced from an open position into a closed position in which the closure member covers or surrounds an object in order to capture, hold, immobilise and/or retain that part such as to provide stability to the object and/or resist forces acting on the object.

BRIEF DESCRIPTION OF THE DRAWINGS

The present invention will now be described with reference to the accompanying drawings, in which:

FIG. 1a illustrates an end elevation of a preferred embodiment of a stabilisation system according to the invention, in an un-deployed state and with a closure member in an open position;

FIG. 1b illustrates a side elevation of the stabilisation system of FIG. 1a.

FIG. 2a illustrates the stabilisation system in a deployed state anchored to a tissue substrate and having a catheter secured therein but with the closure member in the open position;

FIG. 2b illustrates a side elevation of the arrangement illustrated in FIG. 2a;

FIG. 3a illustrates an end elevation of the stabilisation system with the closure member in a closed position capturing the catheter within the stabilisation system;

FIG. 3b illustrates a side elevation of the arrangement of FIG. 3a.

FIG. 4a illustrates a plan elevation from above of FIG. 1a;

FIG. 5a illustrates a side elevation of FIG. 4a;

FIG. 6a illustrates a plan view from below of FIGS. 4a and 5a;

FIG. 7a illustrates side elevation of the stabilisation system in an un-deployed state with the closure member opened;

FIG. 7b illustrates a sectioned side elevation of FIG. 7a;

FIG. 8a illustrates side elevation of the stabilisation system in a deployed state with the closure member opened;

FIG. 8b illustrates a sectioned elevation of FIG. 8a;

FIG. 9a illustrates a side elevation of the stabilisation system in a deployed state with the closure member closed;

FIG. 9b illustrates a sectioned side elevation of FIG. 9a;

FIG. 10 illustrates a schematic perspective view of a microneedles forming part of the stabilisation system of the invention;

FIG. 11 illustrates a schematic side elevation of the microneedle as shown in FIG. 10;

FIG. 12a illustrates a plan view from above of an alternative embodiment of the stabilisation system in an un-deployed state with the closure member opened;

FIG. 12b illustrates the stabilisation system of FIG. 12 in a deployed state with the closure member opened;

FIG. 13a illustrates a side elevation of FIG. 12a;

FIG. 13b illustrates a side elevation of FIG. 12b;

FIG. 14a illustrates a plan view from beneath of FIGS. 12a and 13a;

FIG. 14b illustrates a plan view from beneath of FIGS. 12b and 13b;

FIG. 15a illustrates a front elevation of the stabilisation system of FIGS. 12-14 with a catheter location therein and the closure member in an open position;

FIG. 15b illustrates a side elevation of FIG. 15a;

FIG. 16a illustrates the arrangement of FIG. 15a with the closure member closed;

FIG. 16b illustrates a side elevation of FIG. 16a;

DETAILED DESCRIPTION OF THE DRAWINGS

Figure 4A:
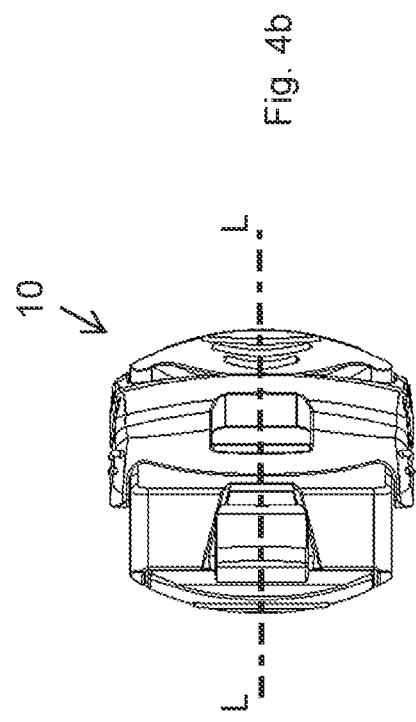
Figure 4B:
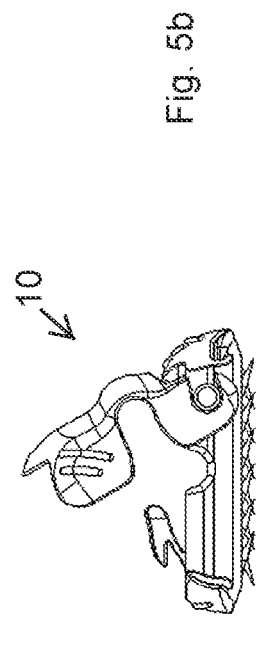
FIG. 4b illustrates plan elevation from above of FIG. 2a without the catheter.
Figure 5A:
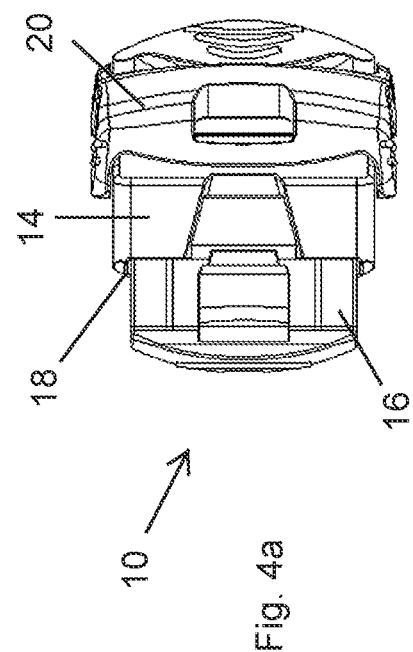
Figure 5B:
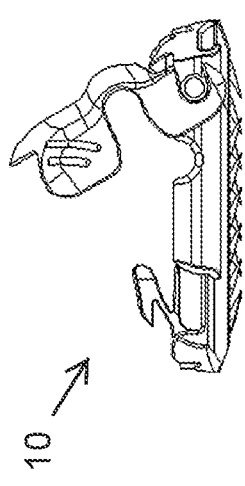
FIG. 5b illustrates a side elevation of FIG. 4b.
Figure 6A:
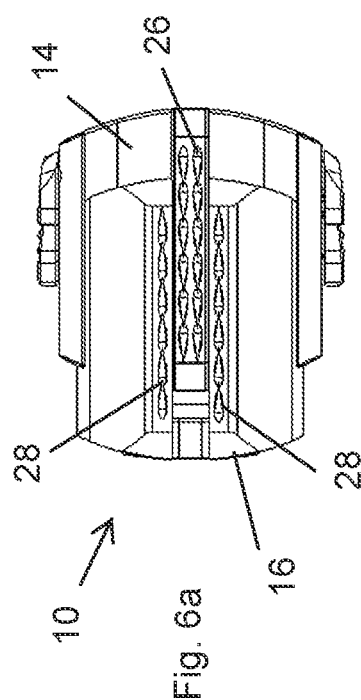
Figure 6B:
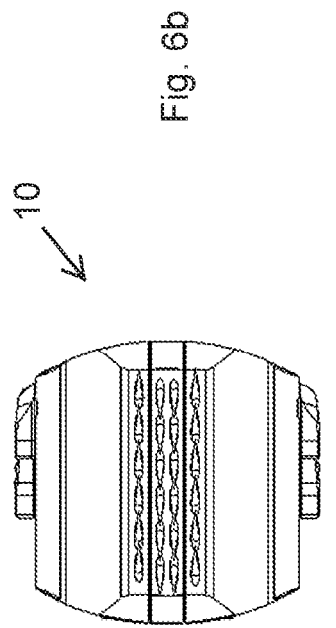
FIG. 6b illustrates a plan view from below of FIGS. 4b and 5b.

Referring now to FIGS. 1 to 11 of the accompanying drawings there is illustrated a stabilisation system for medical devices according to a preferred embodiment of the present invention, generally indicated as 10, for use in anchoring a medical device such as a catheter C to tissue such as the skin S, dura mater, blood vessels, bowel wall or any other tissue located internally or externally of the body. The stabilisation system 10 may be used with tissue, bone, or any other suitable biological substrate, and may be used in applications such as drug delivery, and/or for securing a biosensor or the like.

The stabilisation system 10 comprises a body 12 which may be formed of any suitable material, for example a polymer, metal or a composite of materials, and may for example comprise a bioabsorbable material or a material which is partially or wholly porous in order to promote tissue ingrowth, or which may incorporate one or more channels (not shown) extending from an upper or lateral face through to a tissue contacting face in order to allow a fluid to be flushed through the channels and on to the tissue contact surface for removal of contaminants or for the purpose of disinfection, local anaesthesia, drug delivery, etc. Although not limited to particular dimensions, in the exemplary embodiment illustrated the body 12 has a length in the region of 20 mm as measured along a longitudinal axis LL (see FIG. 4b), a width in the region of 18 mm as measured perpendicular to the longitudinal axis LL, and a thickness in the region of 6 mm perpendicular to both the length and width. These dimensions may of course vary, in particular to suit particular surgical indications. For ease of reference, hereinafter measurements along the length will be referred to as being an "X" coordinate, measurements along the width will be referred to as being a "Y" coordinate and measurements along the depth will be referred to as being a "Z" coordinate.

The body 12 comprises a first section 14 and a second section 16 which are displaceable relative to one another in a first direction and between an un-deployed state as illustrated in FIGS. 1a and 1b and a deployed state as illustrated in FIGS. 2a and 2b, and as will be described in greater detail hereinafter. The first section 14 and the second section 16 are inter-engagable with one another, and in the embodiment illustrated the first section 14 defines a central channel 18 extending longitudinally through the body 12 and is shaped and dimensioned to slidingly receive the second section 16 therein, such that the two sections 14, 16 are effectively telescopically displaceable relative to one another. It will of course be appreciated that any other suitable arrangement or configuration may be employed in order to permit relative movement between the first section 14 and the second section 16. For example it is envisaged that such an arrangement could be a rotational engagement, where the microneedles are arranged in a circumferential array. While in the embodiment illustrated the first and second sections 14, 16 are reversibly displaceable relative to one another, in other embodiments the displacement may be irreversible.

It is also envisaged that embodiments of the invention may be arranged such that the first section 14 and the second section 16 are displaceable independently of one another, for example laterally of one another in comparison to the direction of relative displacement of the sections 14, 16 of the embodiment of FIGS. 1 to 9.

The stabilisation system 10 further comprises a closure member 20 hingedly mounted to the first section 14 via a hinge 22 and displaceable between an open position as illustrated in FIGS. 1a, 1b, 2a and 2b and a closed position as illustrated in FIGS. 3a and 3b. In the open position the closure member 20 permits access to a retention zone in the form of an elongate channel 24 extending transversely across the body 12 relative to the direction of relative displacement of the first and second sections 14, 16. The channel 24 is shaped and dimensioned to receive a catheter C therein, as illustrated in FIGS. 2a, 2b, 3a and 3b although it will be appreciated that the shape and size of the channel 24 may be varied as required in order to accommodate an alternative medical device to the clamped within the stabilisation device 10. The hinge 22 is preferably arranged to allow the closure member 20 to be completely removed from the body 12 if required, but preferably only after the closure member 20 has been placed in the open position. It is however also envisaged that the closure member 20 could be displaceable between the open and closed positions by any other suitable arrangement or displacement, for example the closure member 20 could be slidable linearly or otherwise between the open and closed positions. Further aspects of the configuration and operation of the closure member will be described in detail hereinafter.

Both the first section 14 and the second section 16 each comprise at least one protrusion, and preferably a plurality of the protrusions in the form of twelve microneedles 26 projecting from the first section 14 and twelve microneedles 28 projecting from the second section 16. In each case the microneedles 26, 28 extend from an underside or tissue contacting surface 30 of the respective first section 14 and second section 16. In the embodiment illustrated the microneedles 26 of the first section 14 are arranged in two adjacent parallel rows of six microneedles 26, while those of the second section are arranged in two parallel but spaced apart rows of six microneedles 28, between which rows the microneedles 26 of the first section 14 are located in a parallel orientation. It will however be understood that this configuration is exemplary only and may be varied while still providing the necessary anchoring functionality as hereinafter described.

Each of the microneedles 26, 28 comprise a root which is defined at the tissue contacting surface 30 and a sharpened or pointed tip at a free end of the respective microneedle 26, 28. In the preferred embodiment the microneedles 26, 28 taper uniformly from root to tip although any other suitable configuration may be employed. The uniform taper has however been found to be beneficial in facilitating insertion of the microneedles 26, 28 fully into tissue as hereinafter described in detail.

The microneedles 26, 28 are preferably inclined at an acute angle of inclination a relative to the "X" plane in which the tissue contacting surface 30 lies and extend predominantly in the same direction, from root to tip along a major axis of the microneedles 26, 28, as the direction of relative movement between the first section 14 and the second section 16, also referred to as the "first" direction substantially parallel to the longitudinal axis LL of the body 12. In other words the microneedles 26, 28 can be said to have a greater "X" dimension component than "Z" dimension component.

The microneedles 26, 28 are dimensioned, in the preferred embodiments illustrated, with an axial length from root to tip of approximately 2 mm and a depth or "Z" coordinate length, hereinafter referred to as $L_z$, of approximately 0.9 mm. It has also been found that the preferred angular inclination of the microneedles 26, 28 is between 15° and 50°, more preferably between 20° and 30°, and most preferably approximately 26.5° to the "X" plane. Both the "X" coordinate length $L_x$ and the "Z" coordinate length $L_z$ of each microneedle 26, 28 will vary depending on the angular inclination thereon. It will of course be appreciated that all of these dimensions are exemplary and may vary, in particular to suit different surgical or medical applications or tissue types. The dimensions of the microneedles 26 and 28 could also vary across any given part. For example, those at the perimeter of the respective array could be shorter in length than those at the centre, or vice versa. Similarly, microneedle lengths and aspect ratios could vary in multiple planes The microneedles 26, 28 are arranged and oriented such that the microneedles 26 protruding from the first section 14 extend or point in a direction generally opposite to that of the microneedles 28 protruding from the second section 16. In this way the microneedles 26 essentially face or oppose the microneedles 28. It is also preferable that at least one of the microneedles 26 overlaps with at least one of the microneedles 28 in the "Y" direction, at least when the stabilisation system 10 is in either the deployed and/or un-deployed state, but most preferably when in the deployed state. In addition, it has been found that the greatest anchorage is achieved when the first and second sections 14, 16 have an equal number of microneedles 26, 28. In the embodiment illustrated the first and second sections 14, 16 each comprise twelve microneedles 26, 28, although this number may of course vary. The microneedles 26, 28 are preferably spaced from one another in the "X" direction such that the tip of any one microneedle 26, 28 just reaches or may slightly overlap with the root of the adjacent microneedle 26, 28 or in other words the microneedles are arranged linearly with a spacing between adjacent microneedles 26, 28 of approximately $L_x$. In the preferred embodiment the "Y" spacing between the row of microneedles 26 on the first section 14 and the adjacent row of microneedles 28 on the second section is preferably 1.5 times the "Y" spacing between microneedles 26 of the first section 14. This distance has been found to be effective in avoiding shear damage to the tissue engaged by the stabilisation system 10 in use. The distance that the first and second sections 14, 16 are displaced relative to one another between the undeployed and deployed states is preferably 2.5 times $L_x$, but could also for example be 2 times $L_x$ or less. For example in more elastic tissue the extent of the overlap could be more than 2.5 $L_x$.

The microneedles 26, 28 are arranged to penetrate at least an upper layer or region of the skin S or other tissue to which the system 10 is to be secured, initially by pressing the tissue contacting surface 30 of the body 12 downwardly onto the anchorage site on the skin S in order to push the microneedles 26, 28 into the tissue in a minimally invasive manner. The stabilisation system 10 is applied to the anchor site in the un-deployed state as illustrated in FIGS. 1a and 1b. Once the microneedles 26, 28 are engaged against the skin S the first and second sections 14, 16 are displaced relative to one another into a deployed state as illustrated in FIGS. 2a and 2b. The relative displacement of the first and second sections 14, 16 from the un-deployed to deployed states results in the microneedles 26, 28 being drawn into the skin S as shown in FIGS. 2a and 2b. The distance of this relative displacement is preferably 2.5 times $L_x$, such that the full length of the barbs 26, 28 is drawn into the skin S following a relative displacement of 2 times $L_x$ with the final displacement of 0.5 $L_x$ causing the non-destructive shear deformation of the tissue engaged by the microneedles 26, 28, for example the collagen network in the case of skin S, effectively creating a localised resilient deformation which actively engages the tissue and the microneedles 26, 28 in order to achieve a robust anchorage to the tissue and which is capable of resisting forces in multiple planes as hereinafter described. This distance of displacement has been found to provide sufficient shear deformation of the tissue surrounding or acted on by the microneedles 26, 28 to provide the requisite levels of retention while avoiding any damage to the skin S.

Referring to FIGS. 10 and 11 the system 10 may comprise recesses 31 formed in the tissue contacting surface 30, one directly beneath each of the respective microneedles 26, 28. The recesses 31 facilitate improved anchorage of the first and second sections 14, 16 to the tissue by allowing at least some of the tissue that is displaced by insertion of each microneedles 26, 28 to be received within the respective recess 31, thereby allowing a more complete insertion of each of the microneedles 26, 28. The recess 31 also effectively increases the overall or working length L of each microneedle 26, 28, by exposing the full root which would otherwise be partially encased below the tissue contacting surface 30. The volume of tissue contained, in use, in each recess 31 also serves to resist lateral displacement of the system 10 as the tissue is effectively meshing or interlocking with the body 12. The dimensions of the recess 31 may be varied. FIG. 11 shows a microneedle 26, 28 having a circular cross sectional area. It should however be understood that various other alternative cross-sectional areas may be employed for the microneedles 26, 28.

In addition, while the embodiment described has a tissue contacting base, an alternative embodiment is envisaged in which elongated microneedles exhibit a step change in their diameter, which then effectively defines the tissue contacting surface and a hard shoulder for preventing further advancement of the microneedles into the tissue. In this way, the body could sit in an elevated position relative to the outer tissue layer, and which could be advantageous for drug delivery.

By providing the opposed sets of microneedles 26, 28 the local region of tissue on which the stabilisation system 10 is deployed is effectively captured and lightly compressed and stretched between the overlapping microneedles 26, 28 in order to apply shear deformation and thereby robustly secure the stabilisation system 10 in position. In particular when the stabilisation system 10 is displaced into the deployed state the local region of tissue beneath the body 12 is elastically deformed or compressed and stretched by the displacement of the first section 14 relative to the second section 16, and thus by displacement of the microneedles 26 relative to the preferably overlapping microneedles 28. This elastic shear deformation of the tissue results in a reactive force being applied by the tissue against the microneedles 26, 28 thereby actively engaging and retaining the tissue surrounding the microneedles 26, 28. As a result the microneedles 26, 28 do not need to penetrate to a significant depth to achieve the necessary retention, and may for example be of a length in the region of 0.1-5 mm from root to tip, and have a depth of penetration $L_z$ of less than 1000 μm, although again this dimension may be varied as required. As a result, for skin-based indications, the microneedles 26, 28 can be dimensioned such as not to penetrate to the depth of most pain receptors and blood vessels.

In the preferred embodiment illustrated the skin contacting surface 30 is convex in profile, as can be seen in FIGS. 1a, 2a and 3a, the microneedles 26, 28 preferably being located, in use, at the lowest point on the surface 30, which preferably corresponds with the centreline of the body 12. This convex profile provides a focused contact patch with the skin S or other tissue to which the stabilisation system 10 is to be anchored in order to ensure that the microneedles 26, 28 fully engage with the skin S for maximum penetration and anchorage.

In order to counter the small contact patch created by the convex skin contacting surface 30 the stabilisation device is preferably provided with one or more feet 32 which engage the skin S or other surrounding tissue, preferably outboard of the microneedles 26, 28 defining the contact patch on the skin contacting surface 30, in order to provide one or more outriggers which resist any rolling or pivoting of the body 12 about the contact patch, which could otherwise act to disengage one or more of the microneedles 26, 28. In the preferred embodiment illustrated the stabilisation system 10 comprises four feet 32, two on either side of the body 12, and which are formed integrally with the closure member 20. The feet 32 are located and dimensioned such as to be out of register with the skin S when the closure member 20 is in the open position, and to be rotated downwardly into register with the skin S as the closure member 20 is hinged into the closed position. The pair of feet 32 on each side of the body 12 are separated and defined by a respective guideway in the form of a recess 34 formed in the sidewall of the closure member 20 which recess 34 is positioned to be in alignment with the channel 24 when the closure member 20 is in the closed position, in order to allow the unhindered passage of the catheter C or other medical device through the stabilisation system 10, as illustrated in FIGS. 3a and 3b. This avoids any pinching or other restriction being applied to the catheter C once the closure member 20 is closed against the body 12. The recesses 34 are preferably designed with a flared open end in order to provide a self guiding or aligning function whereby the catheter C will be automatically displaced towards the centre of the recess 34 as the closure member 20 is moved towards the fully closed position in order to ensure that the catheter C is correctly aligned with the channel 24. The closure member 20 may optionally be elongated (not shown) on one or both sides, in the direction in which the catheter C extends, thereby elongating the feet 32 and recess 34 or one or both sides of the system 10 such as to provide a constraining function to provide additional immobilisation of the catheter and provide increased contact area between the enlarged feet 32 and the skin S beneath.

Referring in particular to FIGS. 7, 8 and 9 in order to secure the closure member 20 in the closed position the stabilisation device 10 is preferably provided with a releasable lock comprising a tab 36 formed integrally with the closure member 20 and a corresponding receiver 38 formed integrally with the second section 16, which when engaged with one another secure the closure member 20 in the closed position. The tab 36 and receiver 38 are preferably positioned relative to one another such that the tab 36 can only be located into the receiver 38 when the second section 16 has been displaced inwardly of the first section 14 into the deployed state as shown in FIGS. 8a, 8b, 9a and 9b. In this way the tab 36 and receiver 38, when engaged with one another, also function to retain the body 12 in the deployed configuration. The stabilisation system 10 is however also provided with a separate locking mechanism comprising a resiliently deformable latch 42 formed integrally with the second section 16, below the receiver 38, and a corresponding lip 42 formed integrally with the first section 14 adjacent the channel 24. The latch 40 and lip 42 are provided in order to secure the first and second sections 14, 16 in the deployed configuration, the latch 40 deforming upwardly from the position shown in FIG. 7b, as the first and second sections 14, 16 are displaced towards one another in the "X" direction, before advancing towards and downwardly over the lip 42 as shown in FIG. 8b in order to prevent the separation of the first and second sections 14, 16.

In order to release the latch 40 from the lip 42 a user can simply draw the receiver 38 upwardly in the "Z" direction which will also draw the integrated latch 40 upwardly out of register with the lip 42. Prior to this the user rotates the closure member 20 into the open position by first releasing the tab 36 and receiver 38 and hinging the closure member 20 upwardly. From the open position the closure member 20 can be further torqued or rotated in order to separate the hinge 22 and allow the closure member 20 to be fully removed from the body 12. It should however be understood that in alternative embodiments or arrangements the closure member 20 may not need to be removed to facilitate disengagement of the first and second sections. In other words the user can leverage the closure member to facilitate disengagement. The user can now manually grip the receiver 38 or the closure member 20 and draw upwardly to separate the latch 40 and lip 42, wherein the user can then grip the hinge 22 and tab 38 and apply opposing loads resulting in separation of the first and second sections 14, 16 with a resulting disengagement of the microneedles 26, 28 from the skin S to allow the stabilisation system 10 to be removed.

Once engaged in position on the skin S or other substrate the stabilisation system 10 can be used as an anchor point via which various functions may be performed, for example anchoring the catheter C, a biosensor or any other suitable surgical or medical devices or systems. It is also envisaged that one or more of the microneedles 26, 28 could be employed for drug delivery, wherein one or more of the microneedles 26, 28 could include one or more lumens to facilitate drug delivery into the tissue penetrated by the microneedles 26, 28.

It is also envisaged that the stabilisation system 10 may be modified for use in securing or stabilising a medical device, again such as a catheter (not shown) which enters through the skin or other tissue in a direction substantially normal to the tissue surface, or in other words in the "Z" direction. In such an "over the site" embodiment the body 12 and potentially the closure member 20 would be required to include openings or apertures permitting the passage of such a catheter or the like to pass through the system 10 in the Z direction, with suitable modifications to allow the closure member 20 to clamp the catheter against the body 12 in order to provide the requisite stabilisation functionality.

Referring now to FIGS. 12 to 16 there is illustrated an alternative embodiment of a stabilisation system according to the present invention, generally indicated as 110. In this alternative embodiment like components have been accorded like reference numerals and unless otherwise stated perform a like function. In this alternative embodiment the system 110 again comprises a first section 114 and a second section 116 reversibly displaceable relative to one another, along with a closure member 120 which is displaceable between an open position as illustrated in FIGS. 12a, 12b, 13a and 13b and a closed position as illustrates in FIGS. 16a and 16b. As with the previous embodiment the system 110 is operable to allow the closure member 120 to be locked in the closed position only when the first and second sections 114; 116 have been displaced relative to one another into the deployed configuration, and locking the closure member 120 in the closed positions also acts to lock the first and section sections 114; 116 relative to one another.

Unlike the first embodiment the stabilisation system 110 comprises a tissue contacting surface 130 which defines a pair of spaced apart contact patches which each include an array of microneedles 126 extending from the first section 114 and an array of meshing microneedles 128 extending from the second section 116. By providing these two spaced apart sets of interlocking or meshing microneedles 126; 128, one at either side of the body 112, the stability of the system 110 is improved, and thus the stabilising feet of the first embodiment can be omitted as the functionality of the feet is achieved by means of the spacing apart of the sets of microneedles 126; 128. This configuration of stabilisation system may be particularly suited to the above mentioned "over the site" applications in which the stabilisation system 110 would sit over the site of entry/egress of the catheter or other medical device through the skin. The pair of spaced apart arrays of meshing microneedles 126, 128 would sit on either side of the entry site, with a "Z" direction aperture being provided in the body 112 and closure member 120 in order to facilitate passage of the catheter or other medical device.

It is also envisaged that embodiments of the stabilisation system of the invention, in particular for such "over the site" applications, may include two sets of interlocking microneedles (not shown) which are independently displaceable between the undeployed and deployed states, and which would again preferably be joined by a bridging member or the like, which would also serve to constrain the catheter or other medical device. The two sets of microneedles may be displaceable in different directions between the undeployed and deployed states, for example perpendicular to one another, one in the "X" direction and the other in the "Y" direction.

Cadaveric Testing

The anchorage strength of a prototype embodiment of the microneedle-based stabilisation system of the invention was assessed on human cadavers and compared to that achieved by the SecurAcath® (Interrad, Inc, USA) device when securing a 7Fr (2.33 mm diameter) intravenous (IV) line. Stainless steel (316L) prototypes of the embodiment 110 exhibiting two microneedle arrays positioned at opposing ends of the device were generated using a 3D metal printer (DMLM, Concept Laser MLab, Concept Laser, GE) and subsequently electropolished (E972 Electropolish, Best Technology Model 1085-15), rinsed in de-ionised water and sonicated in Isopropyl Alcohol (IPA). The articulated closure member or lid was prototyped in a PMMA- based resin (Clear Resin V4) using the Form2 SLA 3D printer (Form Labs, USA).

A 500 pm layer of PDMS (Silicone, Platsil 7135, Mould-Life) was applied to the catheter- contacting surface of the articulating lid and body component using custom-designed master moulds (Form2, engaged with the parts. This was undertaken to increase the frictional resistance between the catheter and stabilisation system prototype.

The application of the Sylgard PMDS layer to the catheter-contacting surfaces of the device was undertaken using custom-made mould frames. 1.8 mm titanium Kirshchner wires were passed through recesses in each of the mould frames to mimic the path of the catheter, which were then engaged with the respective parts. Each assembly was dip-coated in a liquid agent (Inhibit X, Smooth-On Inc., Macungie, PA, USA) to protect against cure inhibition. The monomer was then mixed with the platinum initiator, the mixture vacuum-degassed, centrifuged and poured into the moulds to the level of centre of the titanium wire. The assemblies were placed in an oven at 60 degrees for 12 hours and then demoulded.

The prototypes (alternate embodiment and comparator) were then used to anchor 7Fr indwelling catheters applied bilaterally to the upper arms of two human cadavers, in which braided suture was applied to each of the catheter hubs and passed over the distal hook of a SON capacity hand-held force gauge (FK50, Sauter, Germany). Using this setup, axial load applied manually to the catheter was gradually increased until failure of the fixation was achieved. Slippage of the catheter relative to the stabilisation system occurred at 24N and 23N of axial loading for the alternate embodiment and SecurAcath® device, respectively. Needle holders were then applied to the catheter, providing a hard abutment, and testing repeated. The SecurAcath® device detached from the skin at 25N, whilst the prototype system was capable of withstanding in excess of SON of axial loading (exceeding the capacity of the load cell).

Figure 17:
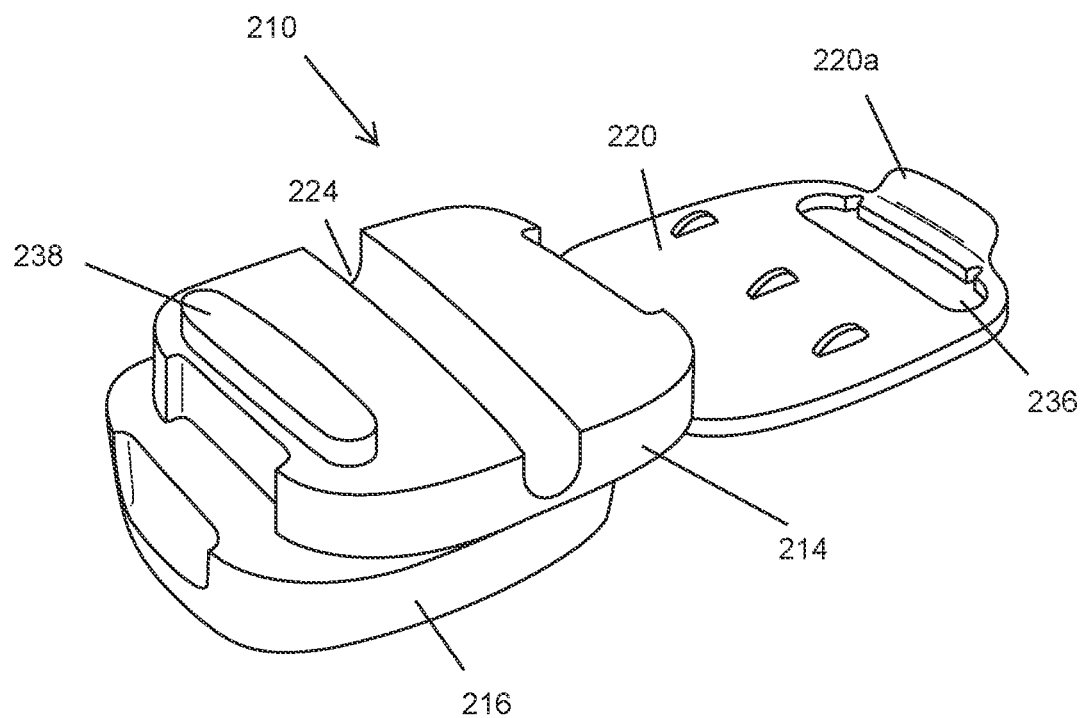
FIG. 17 illustrates a perspective view of a further alternative embodiment of the stabilisation system of the invention in an un-deployed state with a closure member opened to expose a retention zone.
Figure 18:
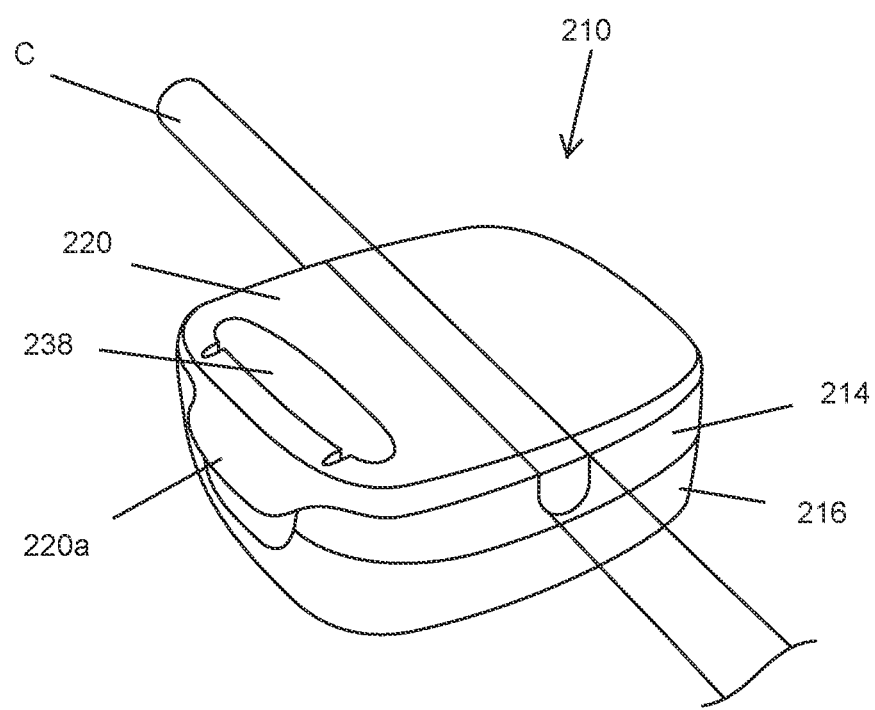
FIG. 18 illustrates the stabilisation system of FIG. 17 in a deployed state and with the closure member closed.

Referring now to FIGS. 17 and 18 there is illustrated a stabilisation system for medical devices according to an alternative embodiment of the present invention, generally indicated as 210, for use in anchoring a medical device such as a catheter C to tissue such as the skin, dura mater, blood vessels, bowel wall or any other tissue located internally or externally of the body. The stabilisation system 210 may again be used with tissue, bone, or any other suitable biological substrate, and may be used in applications such as drug delivery, and/or for securing a biosensor (not shown) or the like. In this alternative embodiment like components have been accorded like reference numerals and unless otherwise stated perform a like function.

Figure 19:
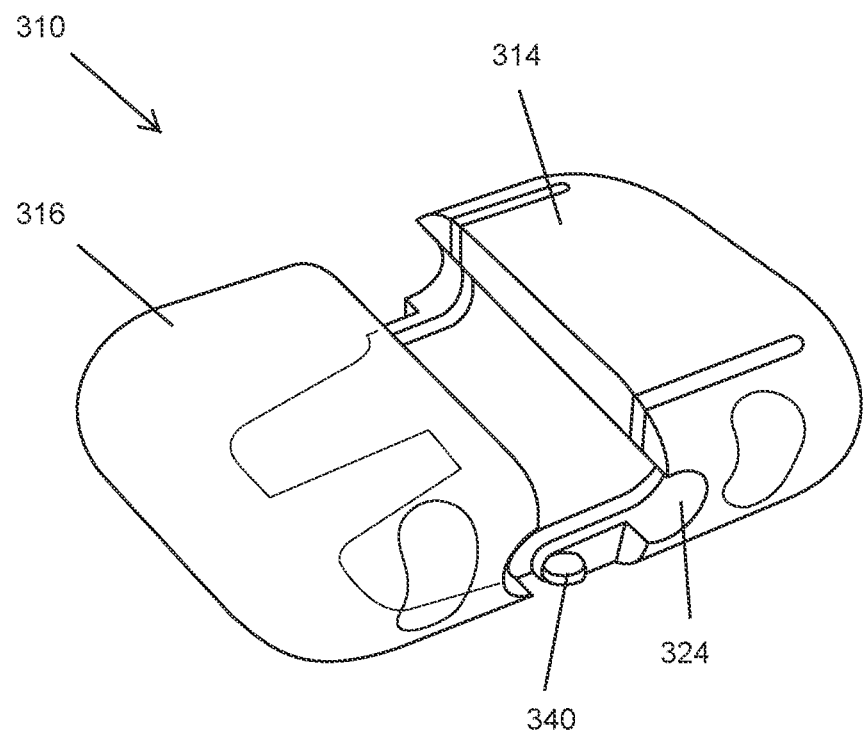
FIG. 19 illustrates a perspective view of a further alternative embodiment of the stabilisation system of the invention in an un-deployed state with a closure member opened to expose a retention zone.
Figure 20:
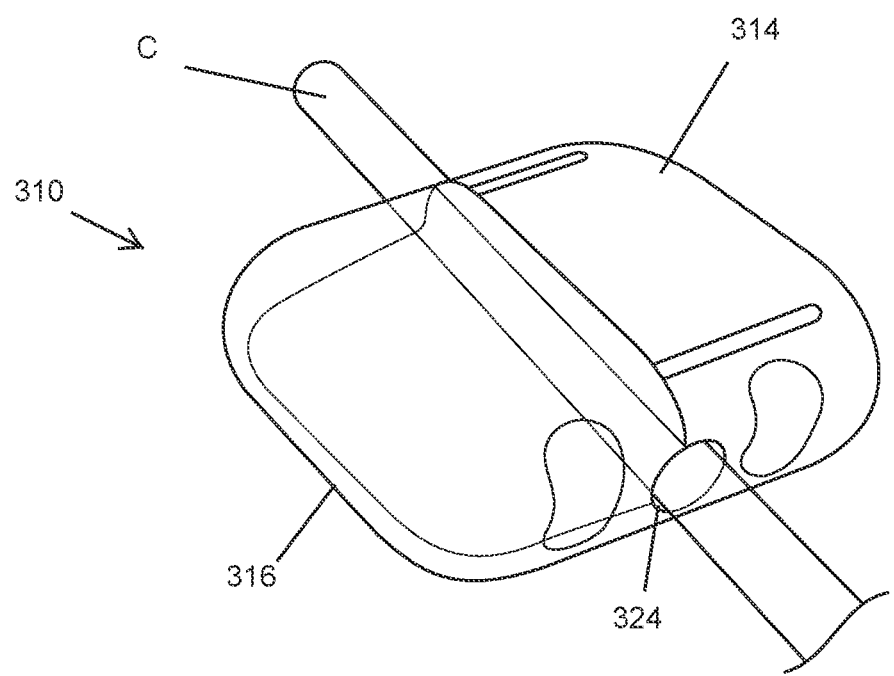
FIG. 20 illustrates the stabilisation system of FIG. 19 in a deployed state and with the closure member closed.

The stabilisation system 210 comprises a first section 214 and a second section 216 reversibly displaceable relative to one another, along with a closure member 220 which is displaceable between an open position as illustrated in FIG. 19 and a closed position as illustrates in FIG. 20. A retention zone in the form of an elongate channel 224 is provided in an upper face of the first section 214, and in the embodiment illustrated in particularly shaped and dimensioned to receive a portion or length of a catheter therein. It is however to be understood that the retention zone could be arranged to receive any other suitable medical device or a portion thereof, or could be adapted for reversibly coupling a connector (not shown) or the like secured to or formed integrally with the medical device. For example a sleeve (not shown) could be provided that is located about a catheter, which sleeve is shaped and/or otherwise adapted for coupling with the retention zone. In this way multiple devices could be coupled to the same stabilisation system 210. The closure member 220 overlies the channel 224 when in the closed position.

As with the previous embodiments, both the first and second sections 214; 216 include an array of protrusions (not shown) in the form of microneedles projecting from an underside or tissue contacting surface of the respective first section 214 and second section 216. The microneedles may be arranged in any suitable configuration that provides the previously described functionality, and for example may be arranged in two adjacent parallel rows of six microneedles on the underside of the first section 214, while those of the second section 216 are arranged in two parallel but spaced apart rows of six microneedles, between which rows the microneedles of the first section 214 are located in a parallel orientation. It will however be understood that this configuration is exemplary only and may be varied while still providing the necessary anchoring functionality.

Each of the microneedles comprises a root which is defined at the tissue contacting surface and a sharpened or pointed tip at a free end of the respective microneedle. The microneedles preferably taper uniformly from root to tip although any other suitable configuration may be employed. The uniform taper has however been found to be beneficial in facilitating insertion of the microneedles fully into tissue.

The microneedles are again preferably inclined at an acute angle of inclination relative to the "X" plane in which the tissue contacting surface lies and extend predominantly in the same direction, from root to tip along a major axis of the microneedles, as the direction of relative movement between the first section 214 and the second section 216, also referred to as the "first" direction. In other words the microneedles can be said to have a greater "X" dimension component than "Z" dimension component.

The microneedles are arranged and oriented such that the microneedles protruding from the first section 214 extend or point in a direction generally opposite to that of the microneedles protruding from the second section 216. In this way the microneedles of the first section 214 essentially face or oppose the microneedles of the second section 216. It is also preferable that at least one of the microneedles of the first section 214 overlaps with at least one of the microneedles of the second section 216 in the "Y" direction, at least when the stabilisation system 210 is in either the deployed and/or un-deployed state, but most preferably when in the deployed state. In addition, it has been found that the greatest anchorage is achieved when the first and second sections 214, 216 have an equal number of microneedles.

As with the previous embodiments the stabilisation system 210 is operable to allow the closure member 220 to be locked in the closed position only when the first and second sections 214; 216 have been displaced relative to one another into the deployed configuration, and locking the closure member 220 in the closed positions also acts to lock the first and section sections 214; 216 relative to one another. The first and second sections 214; 216 are stacked above one another, with the first section 214 being located above the second section 216, although a portion of the first section 214 passes through a suitable channel or opening (not shown) in the second section 216 such that the underside or tissue contact face or surface (not shown) of the first and second sections 214; 216 are substantially coplanar with one another. The first and second sections are displaceable laterally relative to one another in order to effect displacement between the undeployed state as illustrated in FIG. 19 and the deployed state as illustrated in FIG. 20, as hereinbefore described with reference to the previous embodiments.

The closure member 220 comprises a tab 220a in order to facilitate the improved manipulation of the closure member 220 between the open and closed positions. The tab 220a may optionally be configured as a frangible component so as to break away from the closure member 220 on opening in order to ensure that the stabilisation system 210 is not re-used.

In addition the stabilisation system comprises a lock defined by an upstanding lug 238 which can be received within a correspondingly shaped and dimensioned window 236 in the closure member 220, but only when the first and second sections have been displaced into the deployed state, following which the closure member is moved from the open to the closed position. With the lug 238 captured within the window 236 the first and second sections 214; 216 are locked in the deployed state.

Referring now to FIGS. 19 and 20 there is illustrated a stabilisation system for medical devices according to a further alternative embodiment of the present invention, generally indicated as 310, for use in anchoring a medical device such as a catheter C to tissue such as the skin, dura mater, blood vessels, bowel wall or any other tissue located internally or externally of the body. The stabilisation system 310 may again be used with tissue, bone, or any other suitable biological substrate, and may be used in applications such as drug delivery, and/or for securing a biosensor (not shown) or the like. In this alternative embodiment like components have been accorded like reference numerals and unless otherwise stated perform a like function.

The stabilisation system 310 comprises a first section 314 and a second section 316 reversibly displaceable relative to one another, in order to move the system 310 between the undeployed state as illustrated in FIG. 19 and a deployed state as illustrated in FIG. 20. As with all previous embodiments the sections 314; 316 each comprise an array of microneedles (not shown) on a tissue contacting surface, the configuration and operation of which are as with the previous embodiments and no further description of this aspect is therefore considered necessary.

In this embodiment the sections 314; 316 are facing one another and slidable towards and away from one another between the undeployed and deployed states. Opposing faces of the sections 314; 316 are contoured to each define a portion of a retention zone in the form of a channel 324 which is open when the system 310 is in the undeployed state and closed when in the deployed state. A medical device such as a catheter C can therefore be located in the retention zone when the system 310 is in the undeployed state, and the action of displacing the sections 314; 316 towards one another simultaneously displaces the system 10 into the deployed state and closes the channel 324 in order to capture the catheter C therein. As a result, the opposing faces of the sections 314; 316 effectively define a closure member of the system 310, thereby negating the requirement for a separate hinged or otherwise articulated closure member as comprised in the previous embodiments. The closure member is therefore an integral part of the first and second sections 314; 316. An opposed pair of deformable latches 340 (only one visible in FIG. 19) are provided on the first section 314 and which engage a corresponding shoulder (not shown) on the second section 316 in order to lock the sections 314; 316 together. Inward manual pressure applied to either side of the first section 314 will act to reversibly deform the latches 340 inwardly to disengage from the respective shoulder in order to allow the sections 314; 316 to be displaced into the un-deployed state.

Figure 21:
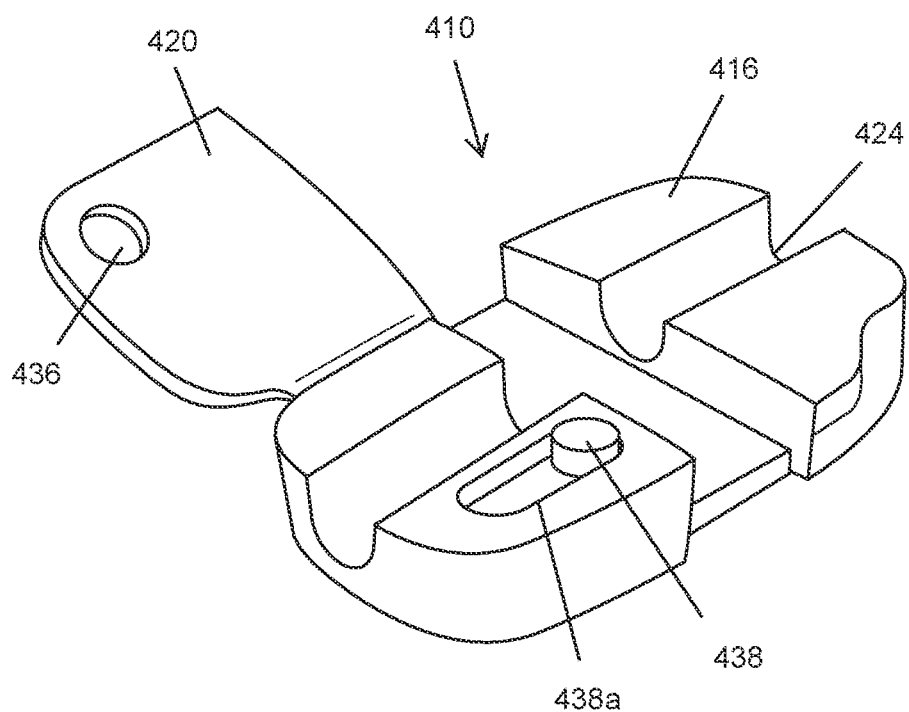
FIG. 21 illustrates a perspective view of a further alternative embodiment of the stabilisation system of the invention in an un-deployed state with a closure member opened to expose a retention zone.
Figure 22:
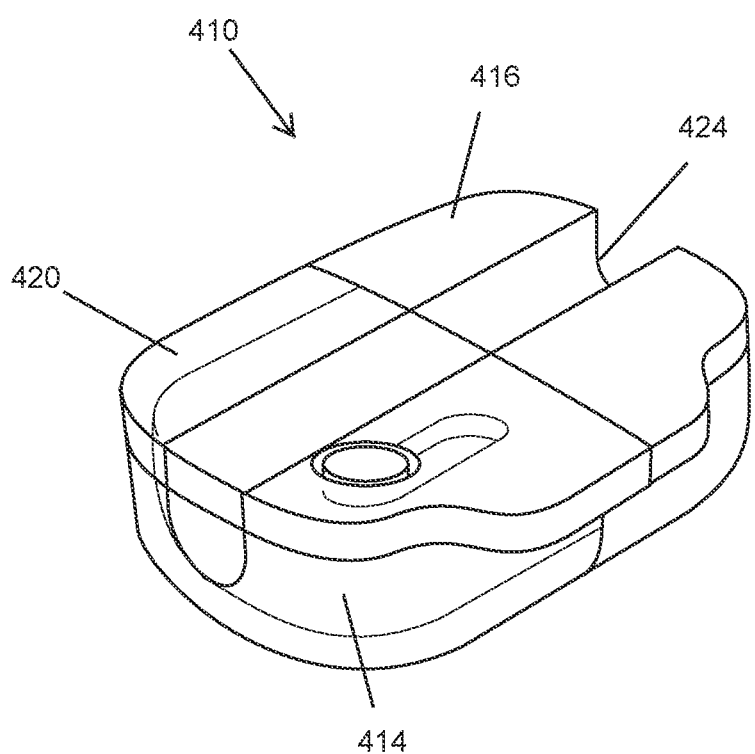
FIG. 22 illustrates the stabilisation system of FIG. 21 in a deployed state and with the closure member closed.

Referring now to FIGS. 21 and 22 there is illustrated a stabilisation system for medical devices according to another alternative embodiment of the present invention, generally indicated as 410, for use in anchoring a medical device such as a catheter C to tissue such as the skin, dura mater, blood vessels, bowel wall or any other tissue located internally or externally of the body. The stabilisation system 410 may be used with tissue, bone, or any other suitable biological substrate, and may be used in applications such as drug delivery, and/or for securing a biosensor (not shown) or the like. In this alternative embodiment like components have been accorded like reference numerals and unless otherwise stated perform a like function.

Figure 23:
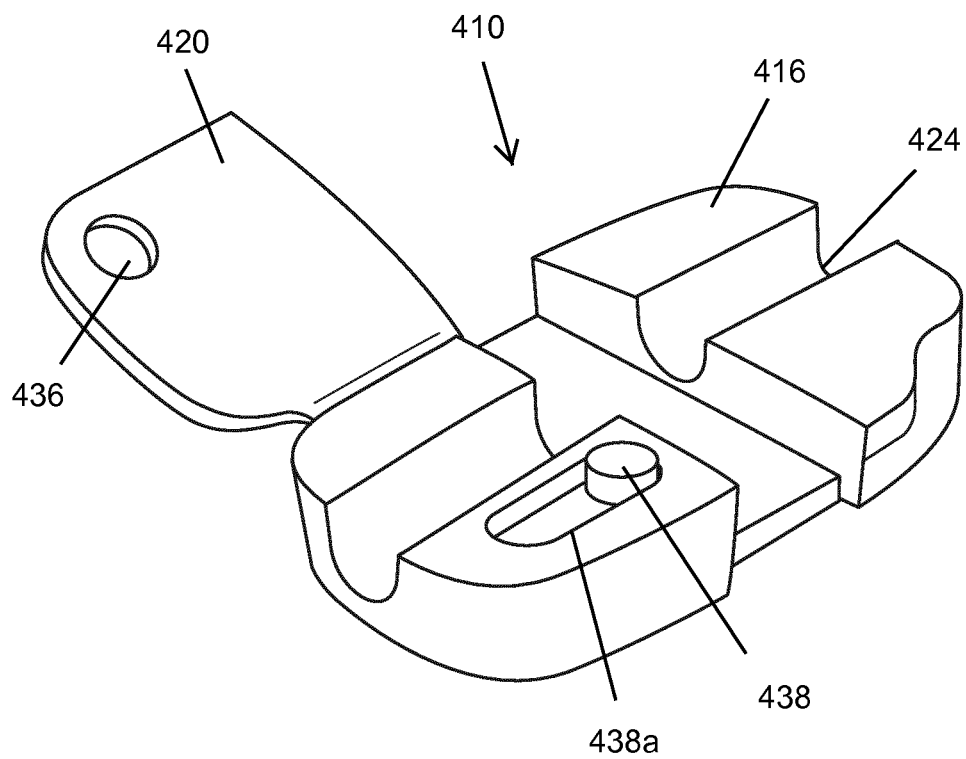
FIG. 23 illustrates a perspective view of a further alternative embodiment of the stabilisation system of the invention in an un-deployed state with a closure member opened to expose a retention zone.
Figure 24:
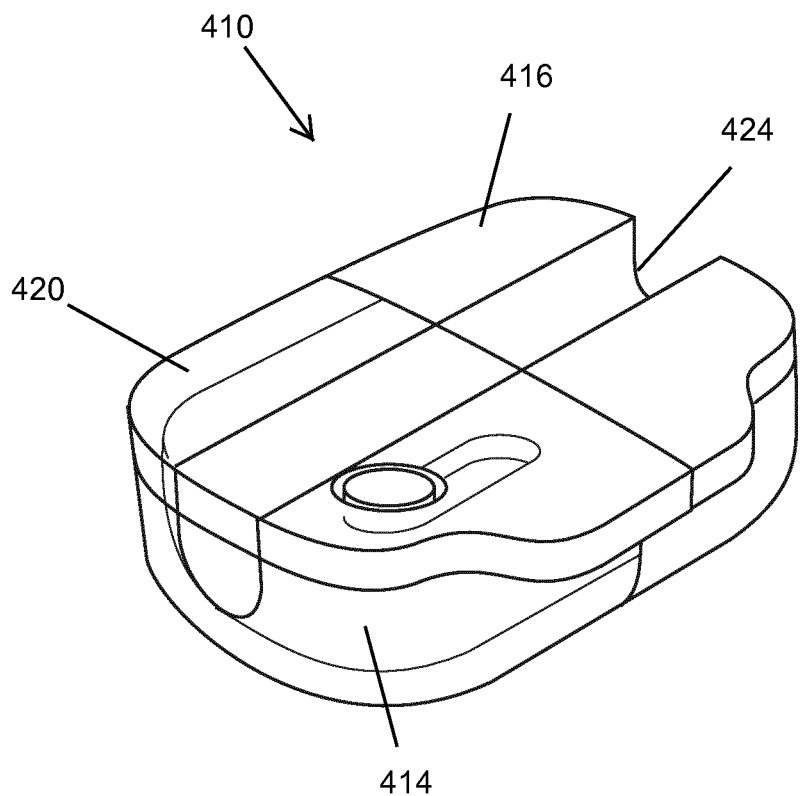
FIG. 24 illustrates the stabilisation system of FIG. 23 in a deployed state and with the closure member closed.

The stabilisation system 410 comprises a first section 414 and a second section 416 reversibly displaceable relative to one another, in order to move the system 410 between the undeployed state as illustrated in FIG. 23 and a deployed state as illustrated in FIG. 24. As with all previous embodiments the sections 414; 416 each comprise an array of microneedles (not shown) on a tissue contacting surface, the configuration and operation of which are as with the previous embodiments and no further description of this aspect is therefore considered necessary.

A retention zone in the form of a channel 424 is provided extending through an upper face of both the first and second sections 414; 416, and parallel to the direction in which the sections are displaced between the undeployed and deployed states.

The system 410 further comprises a closure member 420 which is hingedly mounted to the first section 414 and displaceable between an open position as shown in FIG. 23, in which position the section of the channel 424 on the first section 414 is open in order to allow a catheter or other medical device to be located therein. The first and second sections 414; 416 are then displaced towards one another into the deployed state, thus engaging the system 410 with the underlying tissue, at which point the closure member 420 is moved into the closed position in order to capture the catheter therein. When in the closed position the closure member 420 preferably overhangs the first section 414 opposite the hinged side of the closure member 420 in order to provide oppositional purchase for opening and closing the closure member 420.

The stabilisation system 410 incorporates a lock comprising a lug 438 formed in the second section 416 and captured within an elongate slot 438a formed in the first section 414. The lock additionally comprises a window 436 formed in the closure member and shaped and dimensioned to receive the lug 438 therein, but only when the first and second sections 414; 416 are in the deployed state. Thus when the closure member 420 is hinged down over the channel 420 and into the closed position the lug 438 is captured by the window 436 thereby preventing the sections 414; 416 from being displaced into the undeployed state.

It will therefore be appreciated that the stabilisation system 10; 110; 210; 310; 410 described and shown provides a small yet robust means of quickly and easily securing a medical device such as a catheter or the like to a patients skin or other tissue, which does not cause pain or discomfort during application and use, and which provides improved anchorage strength over many known systems without the problems associated therewith.

The invention claimed is:

1. A stabilisation system for securing medical devices to tissue comprising a main body having a first section and a second section displaceable relative to one another to translate the system between an undeployed state and a deployed state; at least one protrusion projecting from the first section and at least one protrusion projecting from the second section; and a closure member displaceable between an open position exposing a retention zone on the main body and a closed position at least partially occluding the retention zone; wherein the at least one protrusion on the first section and the at least one protrusion on the second section overlap in a first "X" direction and a second "Z" direction substantially perpendicular to the first "X" direction when the system is in the undeployed and the deployed state.

2. The stabilisation system according to claim 1 in which at least one protrusion on the first section or the second section is inclined towards the at least one protrusion on the other of the first section or the second section.

3. The stabilisation system according to claim 1 in which the first section and the second section each define a tissue contacting surface from which the respective at least one protrusion extends.

4. The stabilisation system according to claim 3 in which the tissue contacting surface of the first and/or second section is convex.

5. The stabilisation system according to claim 3 in which the tissue contacting surface of the first section and/or the second section comprises a recess located at or adjacent a root of the respective at least one protrusion.

6. The stabilisation system according to claim 1 comprising one or more feet which are disposed outboard of the at least one protrusion of the first and second sections and are shaped and dimensioned to contact a tissue substrate on which the stabilisation system is deployed.

7. The stabilisation system according to claim 6 wherein the one or more feet comprise one a pair of feet, one located on either side of the at least one protrusion projecting from the first and one of the other foot at the pair of feet located in either side of the at least one protrusion projecting from the second section.

8. The stabilisation system according to claim 6 in which the one or more feet are provided on the closure member.

9. The stabilisation system according to claim 1 comprising a lock operable to releasably secure the closure member in a closed position.

10. The stabilisation system according to claim 9 in which the lock is operable to fix the first and second sections relative to one another.

11. The stabilisation system according to claim 1 in which the closure member comprises a guideway shaped and dimensioned to bias a medical device towards the retention zone as the closure member is displaced from the open to the closed position.

12. The stabilisation system according to claim 1 in which the retention zone comprises an elongate channel.

13. The stabilisation system according to claim 12 in which the elongate channel extends in a direction substantially perpendicular to the first direction.

14. The stabilisation system according to claim 12 in which the elongate channel extends in a direction substantially parallel to the first direction.

15. The stabilisation system according to claim 13 in which the elongate channel extends in a direction substantially perpendicular to the first and the second directions.

16. The stabilisation system according to claim 1 in which the first section defines a slot adapted to at least partially receive the second section therein.

17. The stabilisation system according to claim 1 in which the main body is configured such that the at least one protrusion on the first section and the at least one protrusion on the second section overlap in the second direction when the body is in the deployed state.

18. The stabilisation system according to claim 1 in which each protrusion comprises a microneedle.

19. The stabilisation system according to claim 1 in which the protrusions on both the first and second sections are arranged in a rectangular array.

20. The stabilisation system according to claim 1 in which the body is at least partially formed from a porous material.

21. The stabilisation system according to claim 1 comprising an aperture extending through the body such as to allow a medical component to extend through the stabilisation system from a tissue substrate on which the stabilisation system is deployed.

22. The stabilisation system according to claim 1 in which the closure member is defined by at least a portion of the first section and/or at least a portion of the second section.

23. A method of securing a medical device to tissue with a stabilisation system, the method comprising the steps of inserting at least one protrusion projecting from a first section of a body of the stabilisation system and at least one protrusion projecting from a second section of the stabilisation system into the tissue; displacing in a first "X" direction the first section relative to the second section to translate the stabilisation system from an undeployed state to a deployed state, wherein the at least one protrusion on the first section and the at least one protrusion on the second section effect localised deformation of the tissue surrounding the protrusions when the body is in the deployed state; locating the medical device at least partially within a retention zone on the body before, during or after displacing the stabilisation system into the deployed state; and displacing a closure member of the stabilisation system from an open position exposing the retention zone to a closed position at least partially occluding the retention zone before, during, after or as part of displacing the stabilisation system into the deployed state such as to secure the medical device to the stabilisation system; wherein the at least one protrusion on the first section and the at least one protrusion on the second section overlap in the first "X" direction and a second "Z" direction substantially perpendicular to the first "X" direction when the system is in the undeployed and the deployed state.

* * * * *